United States Patent [19]

Mardones

[11] Patent Number: 5,383,863

[45] Date of Patent: Jan. 24, 1995

[54] ATTACHMENT FOR MAXIMUM SAFETY OF HYPODERMIC SYRINGES

[76] Inventor: Nestor E. Mardones, Pueyrredon 193 - Lomas de Zamora -C.P. (1832) Pcia, de Buenos Aires, Argentina

[21] Appl. No.: 152,297

[22] Filed: Nov. 15, 1993

[51] Int. Cl.⁶ .............................................. A61M 5/00
[52] U.S. Cl. ...................................... 604/198; 604/263
[58] Field of Search ............... 604/110, 198, 192, 263, 604/187, 111

[56] References Cited

U.S. PATENT DOCUMENTS

| | | | |
|---|---|---|---|
| 4,300,678 | 11/1981 | Gyure et al. | 604/111 |
| 4,723,943 | 2/1988 | Spencer | 604/198 |
| 4,810,248 | 3/1989 | Masters et al. | 604/192 |
| 4,966,592 | 10/1990 | Burns et al. | 604/263 |

Primary Examiner—John D. Yasko
Attorney, Agent, or Firm—William H. Maxwell

[57] ABSTRACT

An attachment for standardized hypodermic syringes which is characterized by a protector tube that slides over the syringe and is secured by a catch spring comprised of a split ring that constricts onto the hub that carries the syringe needle and has resilient legs that engage in the longitudinal slot in the protector tube, a detent at an outer end of the slot for retracted postioning of the protector tube exposing the needle, and a lock shoulder (shoulders) at an inner end of the slot for permanent extended positioning of the protector tube covering the needle.

8 Claims, 1 Drawing Sheet

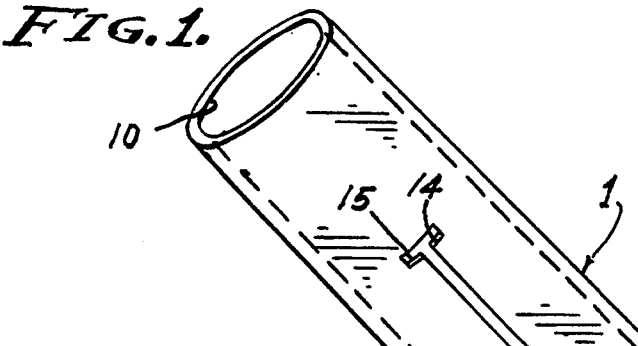
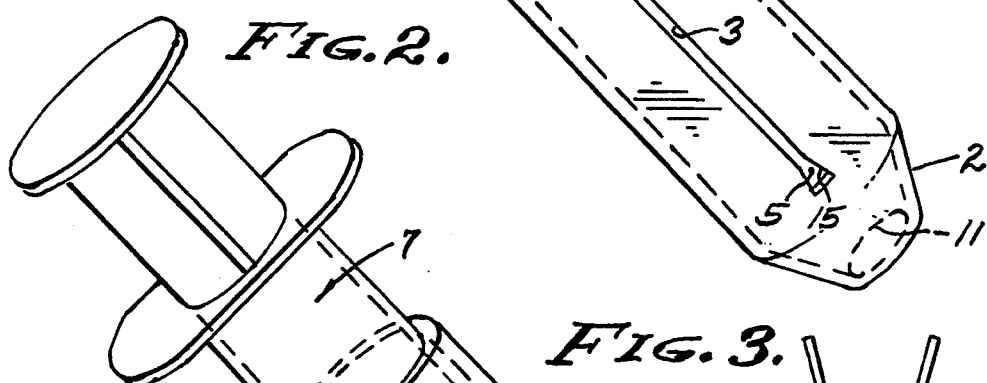
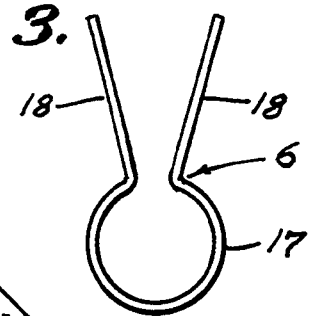
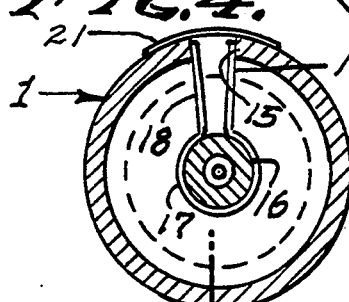
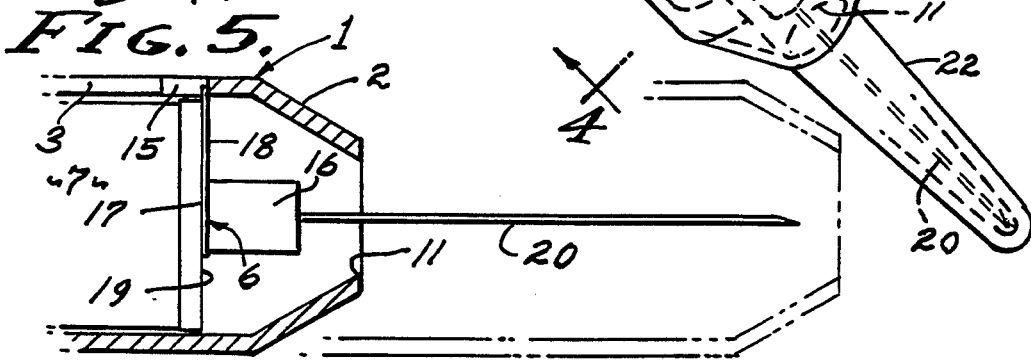

ATTACHMENT FOR MAXIMUM SAFETY OF HYPODERMIC SYRINGES

BACKGROUND OF THE INVENTION

This invention relates to disposable hypodermic syringes, fitted with a sliding telescopic protector and characterized by a unique control and locking system therefor.

In 1989, with the spread of AIDS, the grave potential of increased risk of accidental puncture to medical and paramedical personnel was recognized. It has been reported that another aspect of AIDS constitutes vulnerability due to contamination of the health equipment involved in direct patient assistance, and it is accepted that using a double pair of gloves, mask and apron, avoiding direct contact with blood or discharge, does not diminish accidents with needles. It is reported that punctures with injectable materials constitutes 80% of the medical accidents and not only transmits the AIDS virus but also Hepatitis B virus which causes the most serious forms of that illness. A very high percentage of punctures could be avoided by the utilization of syringes with some protective mechanism. Of all the problems posed by AIDS, this is presently the only one which could have a 90% resolution. It is therefore an object of this invention to solve the problem by achieving a most economically viable and practical solution that maximizes safety.

Of the many ways in which this matter has been dealt, the most common among them is the adoption of a telescopic hood or shield which, when the syringe has been used, slides forward to cover the needle. It is therefore an object of this invention to provide a system characterized by a lock designed to affix the hood in a protective position covering the needle.

Searching logically for a disposable product of the least possible cost gave imeptus, principally in the United States, to inumerable patents, but none of them have reached a stage of mass production. The reason for this is obvious: to attain a non-conventional complex syringe design that requires special materials invariably exceeds pruduction costs which the market cannot accept.

Specifically, U.S. Pat. No. 4,738,663 to shows a hypodermic meedle protector made up of a telescopic tube with both ends open and secured to the syringe cylinder, which maintains a retracted or extended position (alternately), which in the second instance covers the needle. However, the previous forms of locks to keep the protector in the extended position, simple "thorns" of plastic material, could be easily removed and thus accidently expose a potentially contaminated needle.

U.S. Pat. No. 4,747,837 to Hauck shows another tubular hood. In this patent the hood includes a protruded edge of plastic material which fits when in an extended position into a furrow or a circular groove near the end of the discharged hypodermic needle. However, as the hood and edge are necessarily formed in one piece from the same material, it is difficult, industrially to reconcile the rigidity required for the first, with the plasticity required for the second. Furthermore, this system is not adaptable to existing syringes that are excluded for lack of a circular groove.

With reference to U.S. Pat. No. 4,850,994 to Zerbst a hypodermic syringe is shown in which a tubular case is alternately placed in a retracted or an extended position. However, it will be noted that retainers or catches in this case are molded on the syringe cylinder, which results in a weakening of the same. Forthermore, as in all the other prior art patents it requires special syringe manufacture.

U.S. Pat. No. 4,737,144 to Choksi also includes a sliding hood which can be placed in retracted or extended positions. In this patent the lock constitutes an appendage of the hood which fits in a round groove built on the syringe near the hypodermic needle. Similarly, U.S. Pat. No. 4,631,057 to Mitchell shows a sliding case for a hypodermic needle which can be selectively placed in an open or closed position, the lock constituting a ring which in the extended position fits into a special flange of the syringe cylinder, which obviously must be specially manufactured.

In 1991 this inventor was issued Argentina Patent No. 321,339 entitled Accessory Of Prophylaxis For Hypodermic Syringes, which partially overcame the problem here under consideration. That accessory used a sliding telescopic hood with a locking sytem which could be incorporated in any already manufactured syringe. Thus in principle, the product is commercially feasible. Nevertheless until the present time it also has not had wide distribution, since the cost of the accessory nearly duplicates that of the basic syringe, due to the need to rivet a costly non-oxidizable steel lock on each hood. On the other hand, in order to avoid reuse of the syringe or at least the easy separation from the hood, and its recoil to its original position, it necessitates an upgrade of quality in the material used, as it is fixed under pressure, and special care must be taken to the "tip" which is attached to the syringe which is sharp and generates a high degree of friction asgainst the plastic surface and must be reliably riveted, all of which raises the price of mass production.

Therefore, it has required ingenuity to reconcile the three latter suppositions which are contradictory among themselves: simplicity, effectiveness, and manufacturing tolerances.

The foregoing and various other objects and features of this invention will be apparent and fully understood from the following detailed description of the typical preferred form and application thereof, throughout which description reference is made to the the accompanying drawings.

THE DRAWINGS

FIG. 1 is a perspective view of the protector tube, which comprises one of two parts of the attachment.

FIG. 2 is a perspective view of the protector tube installed over a syringe.

FIG. 3 is an enlarged front view of the spring catch means which characterizes this invention, and which comprises one of the two parts of the attachment.

FIG. 4 is an enlarged sectional view taken as indicated by line 4—4 on FIG. 2.

And, FIG. 5 is a fragmentary sectional view taken as indicated by line 5—5 on FIG. 4, showing the extended protective tube in phantom lines.

PREFERRED EMBODIMENT

Referring now to the drawings, there is a transparent tube 1 characterized by the provision of a longitudinal slot 3 having a T formation 4 at its inner end, and having a widened cam formation 5 at its outer extended end.

The protector tube 1 is of cylinder form to slidably telescope over the syringe 7. The inner end of the tube 1 is open at 10 while the opposite extended end of the tube 1 is constricted to a reduced diameter opening 11 corresponding to the diameter of the syringe hub 16 from which the needle 20 projects. As shown, the extended end portion of the tube 1 is a truncated cone 2 that freely passes the needle when retracted as shown in FIG. 2.

The slot 3 is straight and with the T formation 4 and cam formation 5 presents an opening in the side wall of the tube 1, and which is readily molded. The T formation 4 is a transverse extension of the slot 3 that opens circumferentially from opposite sides of the slot 3 and presents a pair of circumferentially spaced stop shoulders 14 faced axially inward toward the open tube end 10. The cam formation 5 is a longitudinally divergent extension of the slot 3 that widens the slot by providing opposed inclined walls 15 to cooperate with a catch member 6 for detent purposes to position the tube 1 before and when the syringe is being used. Accordingly, the shoulders 14 are part of a lock means while the cam walls 15 are part of a detent means.

In accordance with this invention I provide what I term a catch means 6 in the form of a hairpin shaped spring that grips onto the hub 16 of the syringe, releasably engages the cam walls 15 of formation 5 and permanently engages the stop shoulders 14 of the T slot formation 4. As shown in FIG. 3 the catch means 6 is a resilient spring member, preferably of "piano wire" having a split ring-shaped body 17 from which a pair of legs 18 project divergently. The relaxed open diameter of the body 17 passes over the hub 16 and is positioned by a base flange 19 of the hub. Installation of the catch means 6 requires tensioning of the legs 18 by drawing them into parallel relation so as to enter the slot 3, thereby constricting the spring body 17 onto the hub 16. This constriction depresses the body 17 into the hub 16 for fixed positioning thereof. The ends of the spring legs 18 are not exposed beyond the diameter of the tube 1, and are therefore not accessible.

The position of the cam walls 15 is such as to permit spreading of the spring legs 18 when the protective tube 1 is retracted for use of the syringe 7. Alternately, the position of the T formation 4 is such as to permit spreading of the spring legs 18 for locked extended positioning of the protective tube 1 so as to completely cover the needle 20 as shown by phantom lines in FIG. 5.

Installation on the syringe 7 is as follows: The tube 1 is fitted telescopically over the syringe body, and the catch means 6 is inserted to surround the hub 16 against the stop flange 19 of the syringe hub, in such a manner that the legs 18 of the spring remain slidably disposed in the slot 3 offering certain resistance to movement because of the friction generated by its tension.

Once the syringe 7 is used in a conventional manner the protective tube is slid forward to cover the needle 20. Simultaneously, the arms of the catch means 6 are fixedly lodged on the hub 16 by constriction of the spring body 17, the legs 18 being slidable in the slot 3 to enter into the T formation 4 where they engage shoulders 14, thereby immobilizing the protective tube 1 in a position completely covering the needle 20. Having arrived at this position, it is impossible either to have an accident with the needle 20 or to reuse the syringe 7. The length necessary to totally cover the needle, in the case of standardized syringes, is equivalent to the length of the syringe body, its tip and needle included.

It is to be understood that the widening from the narrowest to the widest side shown by the slot at the end of the interior, has the dual purposes of facilitating assembly of the system on one hand, and on the other hand that of maintaining spring legs 18 slightly distended during the shelf life of the syringe and protector assembly, thereby reducing deterioration in the resilience of the catch means 6. There is an anti tamper cover tape 21.

SUMMARY OF THE INVENTION

From the foregoing it will be understood that this invention provides an attachment to a hypodermic syringe, for maximum safety and characterized by the combination of a transparent protective tube telescopically fitted over the body of the syringe, and of a length such that it maintains substantially one quarter part of its length supported upon the syringe, the remainder extending to cover the needle. The protective tube has a cone-shaped outer end with a reduced diameter opening to pass the needle and barely sufficient to receive a protective cap 22. The singular and characteristic positioning slot commences where the cone portion joins the full diameter of the tube and extends ⅔ to ¾ of the tube length and terminates at the T formation. The catch means of resilient wire is disposed in a diametrical transverse plane with its legs perpendicular to the central axis of the syringe, and is solidly fixed onto the hub that carries the syringe needle. The two legs of the catch means remain under tension for constriction of its split ring body in a fixed position on the hub, and for either detented positioning or locked positioning of the prtective tube.

Having described only the typical preferred form and application of my invention, I do not wish to be limited or restricted to the specific details herein set forth, but wish to reserve to myself any modifications or variations that may appear to those skilled in the art, as set forth within the limits of the following claims.

I claim:

1. An attachment for a hypodermic syringe comprised of a hollow cylinder fitted with a plunger and having a sharpened tubular needle for injection or withdrawal of fluids, the attachment exposing the needle when the syringe is used and alternately to permanently cover the needle after the syringe is used, and including;
    a transparent protector tube of cylinder form with an open inner end slidably telescoped over the syringe cylinder and with an open outer end having a retracted position exposing the needle and having an extended position forward of and to cover the needle,
    and catch means in the form of a resilient spring cooperating with a longitudinal slot in the protector tube, the spring being comprised of a split-ring body with a pair of divergent legs brought together by engagement in the longitudinal slot with the split-ring body constricted thereby onto a hub that carries the needle of the syringe, said slot having a means engaged by said catch means for retracted positioning of the protector tube, and having a lock means alternately engaged by said catch means for permanent extended positioning of the protector tube.

2. The attachment for a syringe as set forth in claim 1, wherein the means engaged by the catch means for retracted positioning of the protector tube is a detent means.

3. The attachment for a syringe as set forth in claim 3, wherein the detent means is comprised of divergent opposite side walls of the slot that engage the divergent legs of the catch means.

4. The attachment for a syringe as set forth in claim 1, wherein the lock means alternately engaged by the catch means for permanent extended positioning of the protector tube is a T formation extending the slot transversely at the inner end of the slot.

5. The attachment for a syringe as set forth in claim 1, wherein the lock means alternately engaged by the catch means for permanent extended positioning of the protector tube is a T formation extending the slot transversely at the inner end of the slot and thereby presenting a pair of stop shoulders faced toward the open inner end of the protector tub, said pair of divergent legs of the spring being transversely expansible into stopped engagement with said pair of stop shoulders of the T formation when the protector tube is in an extended position.

6. The attachment for a syringe as set forth in claim 1, wherein the means engaged by the catch means for retracted positioning of the protector tube is a detent means comprised of divergent opposite side walls of the slot that engage the divergent legs of the catch means, and wherein the lock means alternately engaged by the catch means for permanent extended positioning of the protector tube is a T formation extending the slot transversely at the inner end of the slot.

7. The attachment for a syringe as set forth in claim 1, wherein the open outer end of the protector tube is of a diameter to pass a removable protective cap carried over the needle by a hub that carries said needle of the syringe.

8. The attachment for a syringe as set forth in claim 1, wherein a tape covers the slot and obscures the catch means.

* * * * *